United States Patent [19]

Hartenstein et al.

[11] 4,152,326

[45] May 1, 1979

[54] CYCLIC SULPHONYLOXYIMIDES

[75] Inventors: Johannes Hartenstein, Fohrenbuhl; Gerhard Satzinger, Im Mattenbuhl, both of Fed. Rep. of Germany

[73] Assignee: Warner-Lambert Company, Morris Plains, N.J.

[21] Appl. No.: 775,336

[22] Filed: Mar. 7, 1977

[30] Foreign Application Priority Data

Mar. 19, 1976 [DE] Fed. Rep. of Germany ...... 2611690

[51] Int. Cl.$^2$ .................. C07D 221/20; C07D 211/94
[52] U.S. Cl. .................................................. 546/16
[58] Field of Search ..................... 260/293.66, 281 SP

[56] References Cited

U.S. PATENT DOCUMENTS

| | | | |
|---|---|---|---|
| 3,256,276 | 6/1966 | Grogan et al. | 260/293.66 |
| 3,256,277 | 6/1966 | Rice et al. | 260/293.66 |
| 3,432,499 | 3/1969 | Rice et al. | 260/293.66 |

*Primary Examiner*—Henry R. Jiles
*Assistant Examiner*—Robert T. Bond
*Attorney, Agent, or Firm*—Albert H. Graddis; Frank S. Chow

[57] ABSTRACT

The present invention is concerned with new cyclic sulphonyloxyimides and their preparation.

19 Claims, No Drawings

CYCLIC SULPHONYLOXYIMIDES

U.S. Patent application Ser. No. 645,724 filed Dec. 31, 1975, now U.S. Pat. No. 4,024,175 describes compounds of the general formula:

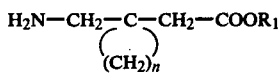

wherein $R_1$ is hydrogen or a lower alkyl radical and n is 4, 5, or 6, as well as the pharmacologically compatible salts thereof. Also described are various processes for the preparation of these compounds which depend upon known "decomposition methods" used for the preparation of primary amines or amino acids.

An important disclosed process is the Lossen rearrangement of appropriate hydroxamic carboxylic acids which, however, suffers from the disadvantage that intermediate products are difficult to isolate in pure form, thus the desired products are also obtained in less pure form.

We have now found that the new cyclic sulphonyloxyimides of the general formula:

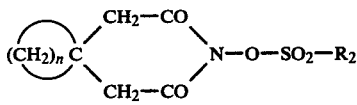

wherein $R_2$ is a saturated, straight-chained, branched or cyclic lower aliphatic radical or an unsubstituted or substituted aryl radical and n is 4, 5 or 6, can be subjected directly to the Lossen rearrangement to obtain especially high yields of formula I compounds in pure form.

When $R_2$ is an aliphatic radical, it preferably contains up to 10 carbon atoms and may optionally bear substituents or carbonyl functions which are non-reactive in the further reaction.

Unlike the hydroxamic carboxylic acids which are difficult to isolate in pure form, the new compounds of general formula (II) useful for the preparation of compounds of general formula (I), are crystalline, stable compounds which, unlike the explosive intermediate compounds formed in the case of the Curtius rearrangement, are harmless. The products of general formula (I) obtained when using the new compounds according to the present invention have a remarkably high degree of purity, whereas large amounts of by-products are formed in the known processes which must be removed in additional purification stages.

Thus, the compounds of general formula (II) enable the Lossen rearrangement to be carried out economically on a large scale.

The compounds of general formula (II) may be prepared by one of the following methods:

(a) O-acylation of a compound of the general formula:

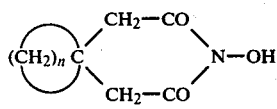

wherein n is 4, 5, or 6 with a reactive derivative of a sulphonic acid of the general formula:

$$HO-SO_2-R_2 \quad (IV)$$

wherein $R_2$ has the same meaning as above; or (b) reaction of a compound of the general formula:

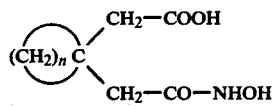

wherein n is 4, 5, or 6, with at least two equivalents of a reactive derivative of a sulphonic acid of general formula (IV), in the presence of an acid-binding agent.

The nature of the $R_2$ radical is not critical having only minor influence on the rearrangement reaction. Thus, $R_2$ can be a methyl or ethyl radical (higher homologues of aliphatic sulphonic acids are at present difficult to obtain and, therefore, can scarcely be used on a technical scale), a cycloalkyl radical, which may also contain a carbonyl function (inexpensive sulphonic acids, such as camphor-sulphonic acid, can be used) or aryl radicals, especially phenyl or naphthyl radicals which can also be substituted by lower alkyl radicals, halogen atoms or nitro groups. Disulphonic acids, for example naphthalene-disulphonic acids, may also be used as compounds of general formula (IV), in which case one molecule of sulphonic acid is esterified with two N-hydroxylimino molecules. Examples of compounds of general formula (IV) include methane-sulphonic acid, ethane-sulphonic acid, benzene-sulphonic acid, p-toluene-sulphonic acid, naphthalene-sulphonic acid, camphor-sulphonic acid, naphthalene-1,5-disulphonic acid, o-nitrophenyl-sulphonic acid, p-bromophenyl-sulphonic acid and p-chlorophenyl-sulphonic acid. Preferred radicals include methyl, ethyl and camphoryl radicals, as well as phenyl and naphthyl radicals which may be substituted by one or more alkyl radicals, preferably methyl radicals, halogen atoms, preferably chlorine atoms, or nitro groups.

The reactive derivatives of the acids of general formula (IV) include the halosulphonic acids, preferably the chlorosulphonic acids, and the sulphonic acid anhydrides.

The compounds of general formula (III), which are also new, are prepared by reacting a hemi-ester of the general formula:

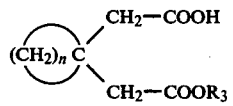

wherein $R_3$ is a lower alkyl of up to 5 carbon atoms and n is 4, 5, or 6 with hydroxylamine at an elevated temperature preferably of from 50° to 100° C.

The compounds of general formula (VI) are known from the literature (J. Chem. Soc., 1929, 713) or may be prepared analogously to the known process by reacting a compound of the general formula:

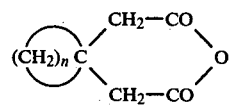

wherein n is 4, 5, or 6, with an equimolar or greater amount of an alcohol containing up to 5 carbon atoms.

The compounds of general formula (V) may be prepared from acid anhydrides of general formula (VII) by reaction, preferably at ambient temperature, with hydroxylamine. The compounds of general formula (VII) are known (J. Chem. Soc., 115, 686/1919; 99, 446; 117, 639/1920).

The O-acylation of the new N-hydroxyimides of general formula (III) is preferably carried out at a temperature of from about 5° to 20° C. with a chloride or anhydride of a sulphonic acid of general formula (IV), either in aqueous or aqueous/alcoholic solution in the presence of an acid binder, for example, an alkali metal carbonate or bicarbonate, preferably sodium bicarbonate, or in an aprotic solvent in the presence of a tertiary amine, for example triethylamine or pyridine.

Reaction (b) is preferably carried out at ambient temperature or below in such a manner that a compound of general formula (V) is reacted with at least 2 equivalents of a reactive acid derivative of general formula (IV) in the presence of an acid-binding agent, for example potassium carbonate or pyridine.

The hydroxylamine is preferably used in aqueous solution, however, other solvents, for example, lower aliphatic alcohols, ethers or aromatic hydrocarbons such as benzene or toluene, can also be used. The compounds of general formula (V) can be converted into compounds of general formula (III) within a period of 0.5 to 2 hours by heating to a temperature of from 50° to 100° C., preferably in the range of from 70° to 80° C. It is also possible to start from compounds of general formula (VII) and to convert these directly into compounds of general formula (III) with hydroxylamine at a temperature above 50° C., preferably of from 70° to 80° C., in which case compounds of general formula (V) are formed and then immediately reacted further.

For the conversion of the compounds into the cyclic amino acids of general formula (I), the cyclic N-sulphonyloxyimides of general formula (II) are subjected to a Lossen rearrangement by heating in aqueous solution in the presence of an equimolar or excess amount of an alkali, preferably a 10% aqueous sodium or potassium hydroxide solution, for 0.5 to 2 hours at 100° C., or by heating in a lower alcohol, for example methanol or ethanol, in the presence of a tertiary amine or an alcoholate at reflux temperature.

In the first case, the reaction mixture, after cooling, is acidified, preferably with concentrated hydrochloric acid, and evaporated. For the separation of inorganic components, the evaporation residue is extracted with absolute ethanol and the amino acid salt, which crystallizes out from the ethanol upon concentrating, is converted into the free amino acid by means of an appropriate basic ion exchanger in the OH form. Only small amounts of lactam are isolated from the mother liquor, which can be converted into the free amino acid. The lactams or urethanes obtained in the case of the second process variant are preferably converted into the corresponding amino acids by means of hydrochloric acid.

The following Examples are given for the purpose of further illustrating the present invention:

EXAMPLE 1

Benzene-sulphonyloxy-1,1-cyclohexane-diacetic acid imide 50 g. 1,1-Cyclohexane-diacetic anhydride was introduced portionwise, while stirring, into an aqueous solution of hydroxylamine, prepared from 23.4 g. hydroxylamine hydrochloride and 21.12 g. sodium carbonate. After completion of the addition, the reaction mixture as heated for 2 hours at 70° C.; an oil separated out. After cooling, the pH was adjusted to 2 with 2N hydrochloric acid and the crystalline precipitate was filtered off with suction. The precipitate was washed with water, taken up in methanol, any undissolved material was removed and, after the addition of water, it was evaporated in a vacuum. There was obtained 45.5 g of 1,1-cyclohexane-diacetic acid N-hydroxyimide; m.p. 104° C.

45.5 g. 1,1-Cyclohexane-diacetic acid N-hydroxyimide in 100 ml. water was mixed with 225 g. of a 10% aqueous solution of sodium carbonate. 29.6 ml (40.75 g) Benzene-sulphonyl chloride was added dropwise to this suspension, while stirring at 5° to 10° C. When the addition was completed, the mixture was stirred for 1.5 hours at ambient temperature. The precipitated product was then filtered off and subsequently washed with methanol. There was obtained 69 g. benzene-sulphonyloxy-1,1-cyclohexane-diacetic acid imide; m.p. 167°-168° C.

EXAMPLE 2

N-Benzene-sulphonyloxy-1,1-cyclopentane-diacetic acid imide

In a manner analogous to that described in Example 1, by the reaction of hydroxylamine with 1,1-cyclopentane-diacetic anhydride, there was obtained 1,1-cyclopentane-diacetic acid N-hydroxyimide (m.p. 70°-74° C.) which, by acylation with benzene-sulphonyl chloride, was converted into benzene-sulphonyloxy-1,1-cyclopentane-diacetic acid imide (m.p. 133°-136° C.).

EXAMPLE 3

N-Benzene-sulphonyloxy-1,1-cycloheptane-diacetic acid imide

In a manner analogous to that described in Example 1, by the reaction of hydroxylamine with 1,1-cycloheptane-diacetic anhydride, there was obtained 1,1-cycloheptane-diacetic acid N-hydroxylimide (m.p. 90°-100° C.) which, by acylation with benzene-sulphonyl chloride, was converted into benzene-sulphonyloxy-1,1-cycloheptane, diacetic acid imide (m.p. 130°-133° C.).

EXAMPLE 4

N-(p-Toluene-sulphonyloxy)-1,1-cyclohexane-diacetic acid imide 2.13 g. p-Toluene-sulphonic acid chloride was added portionwise at 0° C., while stirring, to a solution of 2 g. 1,1-cyclohexane-diacetic acid N-hydroxyimide and 1.6 ml. triethylamine in 35 ml. chloroform. The reaction mixture was stirred overnight at ambient temperature, then poured into water and extracted with methylene chloride. The organic phase was washed with 5% aqueous sodium bicarbonate solution and thereafter with water. It was then dried and evaporated in a vacuum. The residue was recrystallized from chloroform/diethyl ether. There was obtained, in two portions, a total of 2.96 g. (89% of theory) N-(p-toluene-sulphonyloxy)-1,1-cyclohexane-diacetic acid imide (m.p. 133°-135° C.).

In an analogous manner to the previous example, by the reaction of cyclohexane-diacetic acid N-hydroxyimide with methane-sulphonyl chloride, there was obtained N-methane-sulphonyloxy-1,1-cyclohexane-diacetic acid imide (m.p. 77° C.).

Furthermore, by means of the described process, the following compounds can also be prepared: N-methane-sulphonyloxy-1,1-cyclopentane-diacetic acid imide, N-(p-nitrophenylsulphonyloxy)-1,1-cycloheptane-diacetic acid imide, N-ethane-sulphonyloxy-1,1-cyclohexane-diacetic acid imide, N-(p-chlorophenyl-sulphonyloxy)-1,1-cyclohexane-diacetic acid imide, N-(p-bromophenyl-sulphonyloxy)-1,1-cyclopentane-diacetic acid imide, N-1-naphthyl-sulphonyloxy-1,1-cyclohexane-diacetic acid imide, N-1-camphorylsulphonyloxy-1,1-cyclohexane-diacetic acid imide.

EXAMPLE 5

Lossen rearrangement of N-benzene-sulphonyloxy-1,1-cyclohexane-diacetic acid imide Variant A 68.25 g. N-Benzene-sulphonyloxy-1,1-cyclohexane-diacetic acid imide was mixed with 415 ml. 10% aqueous sodium hydroxide solution. The reaction mixture was heated to 100° C., whereby complete solution was gradually obtained. The reaction mixture was then heated for 1 hour, while stirring, at 100° C. and the solution was acidified with concentrated hydrochloric acid. The solution was then evaporated to dryness in a vacuum. The residue was digested with ethanol, inorganic material filtered off and the filtrate evaporated in a vacuum. The solution was again filtered and the filtrate left to stand overnight. 1-aminomethyl-1-cyclohexane-acetic acid crystallized out as the crude benzene-sulphonate (m.p. 163°-167° C.).

The following compounds were prepared in an analogous manner: 1-aminomethyl-1-cyclopentane-acetic acid benzene-sulphonate (m.p. 171°-173° C.); 1-aminomethyl-1-cycloheptane-acetic acid benzene-sulphonate (m.p. 141°-143° C.).

By treatment with a basic ion exchanger, for example "Amberlite" IR-45, in the OH form, the benzene-sulphonate was converted into the free amino acid; by mixing with an alcoholic solution of benzene-sulphonic acid and adding diethyl ether, there was obtained analytically pure 1-aminomethyl-1-cyclohexane-acetic acid benzene-sulphonate (m.p. 165°-168° C.).

Analysis:
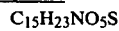

| Calc. : | C 54.69%; | H 7.04%; | N 4.25%; | S 9.73% |
|---|---|---|---|---|
| found : | 54.48%; | 6.85%; | 4.15%; | 9.50% |

The mother liquor, from which the crude benzene-sulphonate has been obtained, was evaporated in a vacuum. The residue was taken up in methylene chloride and washed with 5% aqueous sodium bicarbonate solution and with water. After drying, the solvent was stripped off in a vacuum and the residue subjected to vacuum distillation, to obtain 1-aminomethyl-1-cyclohexane-acetic acid lactam (b.p. 110° C./10$^{-1}$ mm.Hg.; bulbed tube). After recrystallization from diisopropyl ether, the compound had a melting point of 89°-90° C.

By boiling for several hours in semi-concentrated aqueous hydrochloric acid, further amounts of 1-aminomethyl-1-cyclohexane-acetic acid in the form of its hydrochloride (m.p. 123°-133° C., after recrystallization from acetone/water) was obtained.

In a corresponding manner, by the Lossen rearrangement of the N-benzene-sulphonyloxyimides of 1,1-cyclopentane-diacetic acid and of 1,1-cycloheptane-diacetic acid, there was obtained the corresponding amino acids in the form of their benzene-sulphonates.

Variant B 6.75 g. N-Benzene-sulphonyloxy-1,1-cyclohexane-diacetic acid imide was introduced portionwise, while stirring, into an alcoholic solution of sodium ethylate, prepared by dissolving 460 mg. sodium in 50 ml. absolute ethanol and heated under reflux for 2 hours. After cooling, the suspension was poured into water and extracted wit methylene chloride. The organic phase was dried and evaporated to a syrup, crystallization of which from diisopropyl ether gave 1-aminomethyl-1-cyclohexane-acetic acid lactam (m.p. 89°-90° C.), which was then converted into the free amino acid in Variant A.

Variant C 6.75 g. N-Benzene-sulphonyloxy-1,1-cyclohexane-diacetic acid imide was added to a solution of 2.02 g. triethylamine in 50 ml. anhydrous methanol. The reaction mixture was heated to reflux temperature, the initially undissolved material thereby going into solution. After 2 hours, the reaction mixture was allowed to cool and separated between water and methylene chloride. Working up the organic extract in the usual manner and vacuum distillation gave methyl N-carbomethoxy-1-aminomethyl-1-cyclohexane-acetate in the form of a colorless syrup (b.p. 120°-125° C./0.01 mm.Hg.; bulbed tube).

Boiling for 3 hours with semi-concentrated hydrochloric acid, evaporation to dryness and crystallization from acetone/water gave 1-aminomethyl-1-cyclohexane-acetic acid hydrochloride.

Variant D 5.45 g. N-Methane-sulphonyloxy-1,1-cyclohexane-diacetic acid imide was dissolved in 50 ml. methanol and mixed with 2.1 g. triethylamine. The reaction mixture was then boiled under reflux for 3 hours and subsequently worked up according to Variant C. Bulbed tube distillation gave 4.24 g. (87% of theory) methyl N-carbomethoxy-1-aminomethyl-cyclohexane-acetate in the form of a colorless syrup (b.p. 120°-125° C./0.01 mm.Hg.) which was then converted into 1-aminomethyl-1-cyclohexane-acetic acid hydrochloride.

EXAMPLE 6

1-Aminomethyl-1-cycloheptane-acetic-acid hydrochloride

In a manner analogous to Example 5, variant C, N-benzene-sulfonyloxy-1,1-cycloheptane-diacetic acid imide was reacted with triethylamine in methanol giving N-carbomethoxy-1-aminomethyl-1-cycloheptane acetic acid methyl ester as a colorless syrup in a yield of 83% of the theory.

This product was boiled for three hours with semi-concentrated hydrochloric acid, evaporated and recrystallized from acetone diethylether giving 1-aminomethyl-1-cycloheptane acetic acid hydrochloride. Fp. 70°-79° C.

We claim:

1. A cyclic hydroxyimide of the formula:

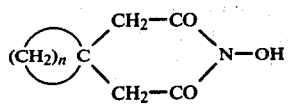

wherein n is 4, 5, or 6.

2. The hydroximide of claim 1 which is 1,1-Cycloheptane-diacetic acid N-hydroxyimide.

3. The hydroximide of claim 1 which is 1,1-Cyclopentane-diacetic acid N-hydroxyimide.

4. The hydroximide of claim 1 which is 1,1-Cyclohexane-diacetic acid N-hydroxyimide.

5. A cyclic sulphonyloxyimide of the formula:

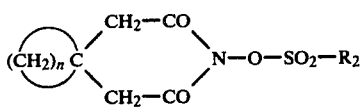
(II)

wherein $R_2$ is selected from the group consisting of methyl, ethyl, camphoryl, phenyl, naphthyl, lower alkyl substituted phenyl, halogen substituted phenyl, nitro substituted phenyl, lower alkyl substituted naphthyl, halogen substituted naphthyl, and nitro substituted naphthyl and wherein n is 4, 5, or 6.

6. A cyclic sulphonyloxyimide according to claim 5 wherein n is 4.

7. The cyclic sulphonyloxyimide of claim 6 which is N-Benzene-sulphonyloxy-1,1-cyclopentane-diacetic acid imide.

8. The cyclic sulphonyloxyimide of claim 6 which is N-Methane-sulphonyloxy-1,1-cyclopentane-diacetic acid imide.

9. The cyclic sulphonyloxyimide of claim 6 which is N-(p-Bromophenyl-sulphonyloxy)-1,1-cyclopentane-diacetic acid imide.

10. A cyclic sulphonyloximide according to claim 5 wherein n is 5.

11. The cyclic sulphonyloxyimide of claim 10 which is Benzene-sulphonyloxy-1,1-cyclohexane-diacetic acid imide.

12. The cyclic sulphonyloxyimide of claim 10 which is N-(p-Toluene-sulphonyloxy)-1,1-cyclohexane-diacetic acid imide.

13. The cyclic sulphonyloxyimide of claim 10 which is N-Methane-sulphonyloxy-1,1-cyclohexane-diacetic acid imide.

14. The cyclic sulphonyloxyimide of claim 10 which is N-Ethane-sulphonyloxy-1,1-cyclohexane-diacetic acid imide.

15. The cyclic sulphonyloxyimide of claim 10 which is N-(p-Chlorophenyl-sulphonyloxy)-1,1-cyclohexane-diacetic acid imide.

16. The cyclic sulphonyloxyimide of clam 10 which is N-1-Naphthyl-sulphonyloxy-1,1-cyclohexane-diacetic acid imide.

17. The cyclic sulphonyloxyimide of claim 10 which is N-1-Camphoryl-sulphonyloxy-1,1-cyclohexane-diacetic acid imide.

18. A cyclic sulphonyloxyimide according to claim 5 wherein n is 6.

19. The cyclic sulphonyloxyimide of claim 18 which is N-(p-Nitrophenylsulphonyloxy)-1,1-cycloheptane-diacetic acid imide.

* * * * *